United States Patent [19]

Gam

[11] Patent Number: 4,635,627
[45] Date of Patent: Jan. 13, 1987

[54] APPARATUS AND METHOD
[75] Inventor: Vivien W. Gam, Shoreview, Minn.
[73] Assignee: Riker Laboratories, Inc., St. Paul, Minn.
[21] Appl. No.: 651,040
[22] Filed: Sep. 13, 1984
[51] Int. Cl.$^4$ .............................................. A61M 16/00
[52] U.S. Cl. .............................. 128/200.14; 128/205.24
[58] Field of Search ................. 128/200.11, 200.24, 128/200.19, 203.12, 203.13, 203.14, 203.25, 204.13, 204.26, 204.25, 205.11, 205.24, 200.14, 204.21, 204.23, 205.18, 204.14; 261/DIG. 65, 55

[56] References Cited

U.S. PATENT DOCUMENTS

| | | | |
|---|---|---|---|
| 1,169,996 | 2/1916 | Prindle | 128/205.24 |
| 2,914,064 | 11/1959 | Sandelowsky | 128/205.24 |
| 3,528,418 | 9/1970 | Grosholz et al. | 128/203.14 |
| 3,741,208 | 6/1973 | Jonsson et al. | 128/204.21 |
| 3,923,056 | 12/1975 | Bingmann et al. | 128/204.21 |
| 3,961,627 | 6/1976 | Ernst et al. | 128/204.21 |
| 4,106,503 | 8/1978 | Rosenthal et al. | 128/194 |
| 4,163,450 | 8/1979 | Kirk et al. | 128/204.23 |
| 4,508,117 | 4/1985 | Rodari | 128/205.24 |

*Primary Examiner*—Henry J. Recla
*Attorney, Agent, or Firm*—Donald M. Sell; James A. Smith; Robert W. Sprague

[57] ABSTRACT

An apparatus for administering a nebulized substance to a subject comprising a nebulizer and a valve assembly which permits continuous and constant flow of pressured gas through the nebulizer even when the apparatus is not being used to administer the substance to a subject. This steady state operation of the nebulizer provides for administration of a controlled dose of the substance. A method for administering a controlled dose to a subject is also described.

3 Claims, 2 Drawing Figures

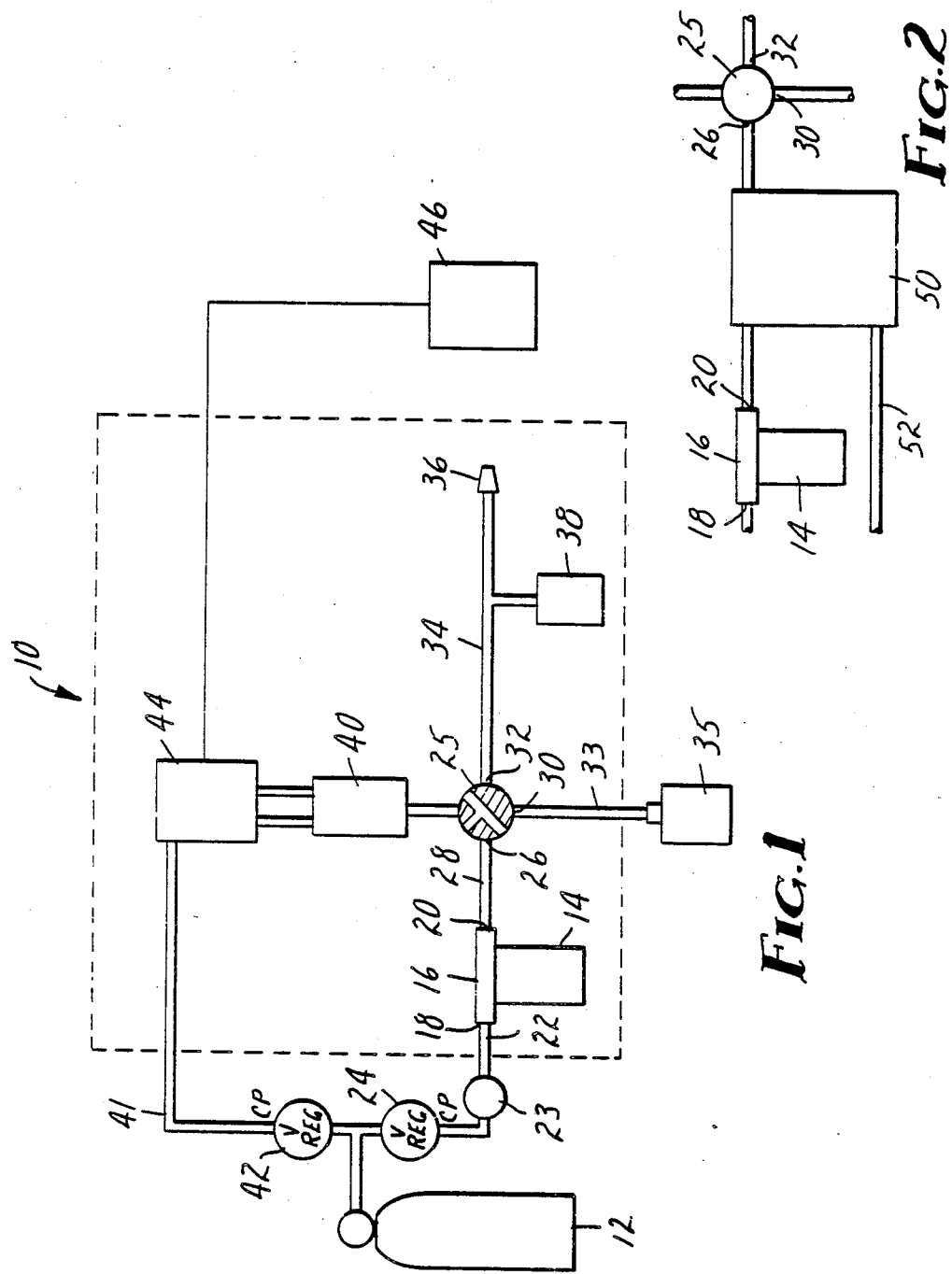

APPARATUS AND METHOD

FIELD OF THE INVENTION

The present invention relates to a nebulizing apparatus and a method for administering a controlled amount of a substance to a subject.

BACKGROUND OF THE INVENTION

The present state of the art for delivering substances to the breathing passages of a subject in an aerosol form includes either formulation in and delivery from an aerosol container comprising a mixture of the substance to be delivered and a compressed gas, or a nebulizer, which utilizes a compressed gas from an outside source to carry the nebulized aerosol to the subject.

A system for delivering a metered dose of a nebulized antigen has been described and claimed by Rosenthal and French, U.S. Pat. No. 4,106,503. This system relies upon control of compressed air fed into a nebulizer to obtain metered dose and includes a detector for sensing initiation of subject inhalation. It is not believed that a conventional nebulizer such as that described in U.S. Pat. No. 4,106,503 permits administration of a closely controlled dose of the substance since the nebulizer of such an apparatus is not given the opportunity to reach steady state operation prior to administration of a dose of the substance. That is, gas flows through the nebulizer only during actual administration of a dose. Upon initiation of gas flow, it is believed that substantial time is required before the size of the aerosolized droplets of the solution or suspension of the substance become essentially constant and to therefore permit administration of a closely controlled dose. The result is that the dose administered to the subject with such a device is not a well-controlled dose.

An apparatus which is capable of administering a closely controlled dose of an aerosol would be desirable such as for use in preliminary drug studies to determine, for example, whether a sufficient amount of an aerosol form of a new drug is absorbed through the lungs for that to be an efficacious route of administration. In studies such as these, the ability to administer a very closely controlled dose of the drug is very important in order for measured blood levels of the drug and the like to be meaningful.

BRIEF SUMMARY OF THE INVENTION

The present invention provides a novel apparatus which is a species of an apparatus claimed in copending application U.S. Ser. No. 650,096, filed of even date and commonly assigned. The apparatus of this invention comprises a nebulizing means having a through opening comprising an inlet and an outlet, the inlet being coupled to a means for providing a supply of gas under pressure. Coupled to the outlet of the nebulizer means is an inlet of a valve means. The valve means further has first and second outlet openings, and portions relatively moveable between a first position at which the portions define a through opening coupled between the inlet of the valve means and the first outlet opening and blocking the second outlet opening, and a second position at which the portions define a through opening coupled between the inlet of the valve means and the second outlet opening and blocking the first outlet opening. The moveable portions of the valve means are normally in the first position. An exhaust means which is coupled to the first outlet opening affords continuous and constant flow of gas through the nebulizing means when the moveable portions of the valve means are in the first position. A delivery means which is coupled to the second outlet opening is adapted to be coupled to the breathing passageway of a subject such as a patient when the moveable portions of the valve means are in the second position. Finally, the apparatus includes an activating means for moving the moveable portions of the valve means from the first position to the second position for a predetermined period, after which the activating means returns the moveable portions back to the first position.

In the apparatus of the present invention, gas flow through the nebulizer need not be interrupted between administrations as is the case with prior art apparatus. As a result, the nebulizer means of the instant apparatus achieves steady state operation such that there is no significant variation in the concentration of substance in the gas flow or in the size of droplets of the aerosolized solution or suspension of the substance. This is in contrast to prior art devices such as that discussed above in which compressed gas flow is necessarily interrupted between administrations, and the nebulizer therefore requires substantial time after compressed air flow is reinitiated for it to reach steady state operation.

The present invention also provides a novel method for administering a controlled dose of a substance to a subject using the apparatus of the invention.

The apparatus and method of the present invention, since they permit administration of a closely controlled dose of an aerosolized substance, are particularly useful in drug studies to determine whether a medicament is efficacious when administered by inhalation in the form of an aerosol.

BRIEF DESCRIPTION OF THE DRAWING

The invention may be further illustrated by reference to the accompanying drawing wherein:

FIG. 1 is a block diagram of a preferred apparatus of the present invention; and FIG. 2 is a block diagram of a portion of an alternative apparatus of the invention.

DETAILED DESCRIPTION OF THE PREFERRED EMBODIMENT

As shown in FIG. 1 of the drawing, apparatus 10 comprises a compressed gas cylinder 12 as the means for providing a supply of gas under pressure. Typically, the gas employed will be air, but any inert, non-toxic gas may be used. Nebulizer 14 having through opening 16, inlet 18 and outlet 20 is coupled to cylinder 12 via high pressure flexible air hose 22 which includes, in its line, a two stage compressed air regulator 24 and a flowmeter 23. Nebulizer 14 is a conventional nebulizer such as a Solo-sphere ® nebulizer, Model PH 2500 (commercially available from Airlife Corp., Montclair, Calif.), a Retec ® nebulizer (commercially available from Cavitron Corp., Long Island City, N.Y.), a Devilbiss Model 880 Ultrasonic Nebulizer (commercially available from the Devilbiss Company), or an Ohio Ball-Jet ® nebulizer (commercially available from Ohio Medical Products, Madison, Wis.). Ball valve 25 is coupled to outlet 20 of nebulizer 14 via inlet 26 using a tube 28 of inert plastic or metal. Ball valve 25 includes first outlet opening 30 and second outlet opening 32, and functions to direct the aerosol generated in nebulizer 14 through only first outlet opening 30 or second outlet opening 32. As will be discussed in greater detail below, ball valve 25 normally directs all aerosol through first outlet opening 30. Coupled to first outlet opening 30 is an exhaust means which comprises conventional tubing 33 which may be connected to a trap such as illustrated water trap 35 to prevent passage of the aerosolized substance into room air. It is the presence of first outlet opening 30 and the exhaust means which permits nebulizer 14 to operate steady state at all times, even between administrations of the aerosol to patients.

A cascade impactor or other dose sampling device by which the aerosolized dose may be scientifically examined may also periodically be connected to the exhaust means. Such devices are used to measure the size distribution, numerical distribution and dose, that is the quantity of the aerosolized substance.

Coupled to second outlet opening 32 is a delivery means which comprises conventional tubing 34, a mouthpiece 36 suitable for permitting coupling of the apparatus with the breathing passages of the subject, and teflon check valve 38. The subject may be, for example, a human being or a laboratory test animal. Teflon check valve 38 is a one-way valve which allows air to enter the apparatus from, the environment so as to be inhaled by the subject, but prevents aerosol and exhaled vapor from passing into the environment.

As indicated above, aerosol normally passes through the exhaust means. When it is desired to administer a dose of the aerosolized substance to a subject, it is an activating means which functions to cause ball valve 25 to direct all aerosol through second outlet opening 32 to the delivery means for a preset period of time, as opposed to directing the aerosol through first outlet opening 30 as it normally does. In the illustrated embodiment, the activating means comprises a pneumatic actuator 40 which is coupled to cylinder 12 via tubing 41 and a two-stage, adjustable pressure compressed air regulator 42 and solenoid pilot valve 44. The activating means further includes an adjustable, single shot delay timer 46 which is activated by a pushbutton (not illustrated). Timer 46, when activated, causes solenoid pilot valve 44 to supply compressed gas to pneumatic actuator 40 so as to cause ball valve 25 to direct aerosol through second outlet opening 32. Thus, it is timer 46 which determines the period of time during which ball valve 25 directs all aerosol through second outlet opening 32 to the delivery means. Typically, timer 46 is set for a period of usually ten seconds or less. Most commonly, timer 46 is set for a period of about 0.1 to 5 seconds.

FIG. 2 shows an alternative apparatus of the present invention wherein aerosol generated in nebulizer 14 passes through mixing chamber 50 where it is mixed with an externally sourced gas prior to passage to ball valve 25. The externally sourced gas is supplied through tube 52 and will generally be controlled by a flowmeter (not illustrated). The externally sourced gas is generally the same as or compatible with the gas carrying the aerosol, and is used to dilute the aerosol and, independently of nebulizer 14, to adjust the concentration of the aerosolized substance. Employment of mixing chamber 50 is advantageous in situations where it is desirable to control particle size via the nebulizer and the concentration of the aerosol in an alternative way.

While the activating means preferably includes a timer such as timer 46 shown in FIG. 1, the activating means may comprise alternative means for controlling the administration of a dose such as a flow meter which, by acting on the valve means, causes initiation of dose release at a certain air velocity associated with subject inhalation and terminates dose release after a predetermined volume of gas has passed through the meter.

The apparatus of the invention may be built to be used as is, or it may be built to be conveniently disassembled between uses. Disassembling and cleaning would allow the same apparatus to be used for delivering various substances.

The various substances which may be delivered via the apparatus of the invention include any substances which form aerosols when nebulized such as atropine and its salts, for example, atropine sulfate; various steroidal compounds such as beclomethasone and dexamethasone; sodium chloride; bronchodilators, for example, rimiterol, epinephrine, isoproterenol, albuterol, metaproterenol, isoetharine and the like; and various materials which are delivered via the pulmonary or nasal route, for example, substances not stable in the gastrointestinal tract, extensively metabolized by the liver or not readily absorbed by other routes. Some examples of the latter types of substances are peptides, hormones, insulin, heparin and the like. Other examples of materials which may be delivered via the apparatus of the invention are allergens, for example, when testing for allergic reactions. Further, the apparatus of the invention may be used for delivering contrast medium for X-rays.

What is claimed is:

1. A device for administering a closely controlled dose of an aerosol, comprising:
    means for providing a supply of gas under pressure,
    nebulizing means having a through opening comprising an inlet and an outlet, said inlet being coupled to said supply of gas,
    valve means having an inlet coupled to the outlet of said nebulizing means, first and second outlet openings, and portions relatively moveable between a first portion at which said portions define a through opening coupled between said inlet of said valve means and said first outlet opening and blocking said second outlet opening, and a second position at which said portions define a through opening coupled between said inlet of said valve means and said second outlet opening and blocking said first outlet opening, said portions normally being in said first position,
    exhaust means coupled to said first outlet opening for affording continuous and constant flow of gas through said nebulizing means when said portions are in said first position.
    delivery means coupled to said second outlet opening adapted to be coupled to the breathing passageway of a subject when said portions are in said second position, and
    activating means for moving said portions from said first position to said second position for a predetermined period, after which said activating means returns said portions back to said first position.

2. A nebulizer apparatus according to claim 1, wherein said valve means is a ball valve.

3. A device for administering a closely controlled dose of an aerosol, comprising:
    means for providing a supply of gas under pressure,
    nebulizing means having a through opening comprising an inlet and an outlet, said inlet being coupled to said supply of gas, valve means having an inlet coupled to the outlet of said nebulizing means, first and second outlet openings, said portions relatively moveable between a first position at which said portions define a through opening coupled between said inlet of said valve means and said first outlet opening and blocking said second outlet opening, and a second position at which said portions define a through opening coupled between said inlet of said valve means and said second outlet opening and blocking said first outlet opening, said portions normally being in said first position, exhaust means coupled to said first outlet opening for affording continuous and constant flow of gas through said nebulizing means when said portions are in said first position, delivery means coupled to said second outlet opening adapted to be coupled to the breathing passageway of a subject when said portions are in said second position, and activating means for moving said portions from said first position to said second position for a predetermined period, after which said activating means returns said portions back to said first position, said activating means including a timer which determines the time said portions are in said second position, and pushbutton means which activates said timer.

* * * * *